(12) United States Patent
Rutter et al.

(10) Patent No.: US 6,475,489 B1
(45) Date of Patent: *Nov. 5, 2002

(54) SYNTHESIS OF HUMAN VIRUS ANTIGENS BY YEAST

(75) Inventors: William J. Rutter, San Francisco, CA (US); Pablo D. T. Valenzuela, San Francisco, CA (US); Benjamin D. Hall, Bellevue, WA (US); Gustav Ammerer, Seattle, WA (US)

(73) Assignee: The Regents of the University of California

( * ) Notice: Subject to any disclaimer, the term of this patent is extended or adjusted under 35 U.S.C. 154(b) by 0 days.

This patent is subject to a terminal disclaimer.

(21) Appl. No.: 08/482,156

(22) Filed: Jun. 7, 1995

Related U.S. Application Data

(63) Continuation of application No. 07/209,504, filed on Jun. 21, 1988, which is a division of application No. 06/821,146, filed on Dec. 12, 1985, now Pat. No. 4,769,238, which is a continuation-in-part of application No. 06/402,330, filed on Jul. 27, 1982, now abandoned, which is a continuation-in-part of application No. 06/289,915, filed on Aug. 4, 1981, now abandoned.

(51) Int. Cl.$^7$ .......................... A61K 39/29; C07K 14/00

(52) U.S. Cl. ................................. 424/189.1; 530/403

(58) Field of Search ........................... 435/320.1, 172.3, 435/254.11, 69.1, 69.3; 536/23.72; 424/227.1, 189.1; 530/403; 930/220; 935/12, 22, 23, 33, 37, 69

(56) References Cited

U.S. PATENT DOCUMENTS

| 4,088,748 A | 5/1978 | McAleer et al. .......... 424/227.1 |
| 4,181,713 A | 1/1980 | McAleer et al. ............ 530/413 |
| 4,264,731 A | 4/1981 | Shine ...................... 435/91.41 |
| 4,415,491 A | 11/1983 | Vyas et al. .................. 530/327 |
| 4,428,941 A | 1/1984 | Galibert et al. ................ 514/2 |
| 4,547,367 A | 10/1985 | Tabor et al. ............. 424/227.1 |
| 4,547,368 A | 10/1985 | Tabor et al. ............. 424/227.1 |
| 4,769,238 A * | 9/1988 | Rutter et al. ............. 424/227.1 |
| 4,803,164 A | 2/1989 | Hitzeman et al. .......... 435/69.1 |
| 5,314,808 A | 5/1994 | Tiollais et al. ............. 435/69.3 |
| 5,591,638 A | 1/1997 | Tiollais et al. ............ 435/320.1 |

FOREIGN PATENT DOCUMENTS

| EP | 0009930 | 4/1980 |
| EP | 0011562 | 5/1980 |
| EP | 0013828 | 8/1980 |
| EP | 0020251 | 12/1980 |
| EP | 0073656 | 3/1983 |
| EP | 0068719 | 5/1983 |
| EP | 0088632 | 9/1983 |
| FR | 2444713 | 7/1980 |
| GB | 2034323 | 4/1980 |
| JP | 58-90517 | 5/1983 |
| JP | 64-86971 | 3/1989 |
| WO | WO 83/01783 | 5/1983 |

OTHER PUBLICATIONS

Cabral et al., "Cellular and humoral immunity in guinea-pigs to 2 major poly peptides derived from hepatitis B surface antigen," *J. Gen. Virol.* (1978) 38:339–350.

Alexander et al., "Establishment of a continuously gowing cell line from primary carcinoma of the liver". *S. Afr. Med. J.*(1976) 50:2124–2128.

Beggs, "Transformation of yeast by replicating hybrid plasmid," *Nature*(1978) 275:104–108.

Beggs et al., "Abnormal expression of chromosomal rabbit beta–globin gene *Saccharomyces cerevisiae*," *Nature*(1980) 283:835–840.

Bennetzen et al., "The primary structure of the *Saccharomyces cerevisiae* gene for alcohol dehydrogenase I," *J. Biol. Chem.*(1982) 257:3018–3025.

Broach et al., "Replication and recombination functions associated with the yeast plasmid 2–MU circle," *Cell*(1980) 21:501–508.

Broach et al., "Transformation in yeast: Development of a hybrid cloning vector and isolation of the CAN 1 gene," *Gene*(1979) 8:121–133.

Charnay et al., "Localization on the viral genome and nucleotide sequence of the gene coding for the two major poly peptides of the hepatitis B surface antigen (HB Ag)," *Nucl. Acid Res.*(1979) 7:335–346.

Charnay et al., "Biosynthesis of hepatitis B virus surface antigen in *Escherichia coli*," *Nature*(1980) 286:893–895.

Christman, "Amplification of expression of hepatitis B surface antigen in 3T3 cells co–transfected with a dominant acting gene and cloned viral DNA," *Proc. Natl. Acad. Sci. USA*(1982) 79:1815–1819.

Dubois et al., "Excretion of hepatitis B surface antigen particles from mouse cells transformed with cloned viral DNA," *Proc. Natl. Acad. Sci. USA*(1980) 77:4549–4553.

(List continued on next page.)

*Primary Examiner*—Karen Cochrane Carlson
(74) *Attorney, Agent, or Firm*—Morrison & Foerster LLP

(57) ABSTRACT

The present invention relates to synthesis of HBsAg in yeast. Yeast expression vectors comprising a yeast promoter, ADH1, have been constructed. The region of the HBV genome coding for the S-protein, excluding a possible 163 amino acid presequence, has been transferred to the yeast expression vector. Using the described yeast vector, the successful synthesis of HBsAg by yeast has been achieved. The product is antigenic (reactive with anti-HBsAg), and a substantial portion is found associated with particles identical in electron microscopic appearance to those found in the serum of HBV-infected patients and in Alexander cells but having a smaller particle size diameter. The HBSAg synthesized by yeast has identical sedimentation behavior to purified, naturally-occurring HBsAq particles purified from Alexander cells as measured by sucrose gradient sedimentation. The present invention demonstrates synthesis and assembly of a higher ordered multi-component structure resulting from expression of a heterologous DNA coding segment in a microorganism.

3 Claims, 6 Drawing Sheets

OTHER PUBLICATIONS

Edman et al., "Integration of hepatitis B virus and their expression in a human hepatoma cell," *Nature*(1980) 286:535–538.

Edman et al., "Synthesis of hepatitis B surface and core antigens in *Escherichia coli*," *Nature*(1981) 291:503–506.

Faye et al., "Deletion mapping of sequences essential for in–vivo transcription of the ISO 1 cytochrome C gene," *Proc. Natl. Acad. Sci. USA*(1981) 78:2258–2262.

Galibert et al., "Nucleotide sequence of the hepatitis B virus genome subtype AYW cloned in *Escherichia coli*," *Nature*(1979) 281:646–650.

Gray et al., "A human hepatoma cell line contains hepatitis B DNA & RNA sequences," *Supramol. Struc.*(1980) 9:281–293.

Gray et al., TCN–UCLA *Symp. Mol. Cell Biol.*(Anim. Virus Genet.) (1980) 18:281–293.

Hartley et al., "Nucleotide sequence of the yeast plasmid," *Nature*(1980) 286:860–865.

Hicks et al., "Genetic transformation in yeast," *Cold Spring Harbor Symp. Quant. Bio.*(1979) 43:1305–1309.

Hinnen et al., "Vectors for cloning in yeast *Saccharomyces cerevisiae*," *Curr. Topics Micro. Imm.*(1982) 96:101–118.

Hitzeman et al., "Expression of a human gene for inferon in yeast," *Nature*(1981) 293:717–722.

Hollenberg, "Cloning with micrometer DNA vectors and the expression of foreign genes in *Saccharomyces cerevisiae*," *Curr. Topics Micro. Imm.*(1982) 96:119–144.

Hollinger et al., "Assay of Australia antigen and antibody employing double antibody and solid phase radio immuno assay techniques and comparison with the passive HEM agglutination methods," *J. Immunol.*(1971) 107:1099–1111.

Klenow et al., "Selective elimination of the exo–nuclease activity of the DNA polymerase from *Escherichia coli* by limited proteolysis," *Proc. Natl. Acad. Sci. USA*(1970) 65:168–175.

Laub et al., "Synthesis of hepatitis B surface antigen in mammalian cells: Expression of the entire gene and the coding region," *J. Virol.*(1983) 48:271–280.

Lerner et al., "Chemically synthesized peptides from the nucleotide sequence of the hepatitis B virus genome: Elicit antibodies reactive with the native envelope protein of dane particles," *Proc. Natl. Acad. Sci. USA*(1981) 78:3403–3407.

Livingston, "Inheritance of the 2 micrometer DNA plasmid from *Saccharomyces*," *Genetics*(1977) 86:73–84.

Macnab et al., "Hepatitis B surface antigen produced by a human hepatoma cell line," *Br. J. Cancer*(1976) 34:509–515.

Grant Application No. R01GM28520–01 to Rutter, "Specific gene expression in eukaryotic organisms" (filing year 1981).

Mishiro et al., "A 49000 dalton poly peptide bearing all antigenic determinants and full immunogenicity of 22 nanometer hepatitis B surface antigen particles," *J. Immunol.*(1980) 124:1589–1593.

Pourcel et al., "Transcription of hepatitis B surface antigen gene in mouse cells transformed with cloned viral DNA," *J. Virol.*(1982) 42:100–105. (pp. 101–105) p. 100 missing.

Skelly et al., "Hepatitis B poly peptide vaccine preparation in micelle form," *Nature*(1981) 290:51–54.

Stinchcomb et al., "Isolation and characterization of a yeast chromosomal replicator," *Nature*(1979) 282:39–43.

Tiollais et al., "Biology of hepatitis B virus," *Science*(1981) 213:406–411.

Valenzuela et al., *Animal Virus Genetics*(1980) Fields et al., eds., Academic Press, New York, pp. 57–70.

Valenzuela, "Structure, identification of the genes and integration of the hepatitis B viral genome". *Rev. Med. Chile*(1981) 109:498–504. English Abstract.

Valenzuela et al., "Nucleotide sequence of the gene coding for the major protein of hepatitis B virus surface antigen," *Nature*(1979) 280:815–819.

Valenzuela et al., "Synthesis and assembly of hepatitis B virus surface antigen particles in yeast *Saccharomyces cerevisiae*," *Nature*(1982) 298:347–350.

Wain–Hobson et al., "Structure and expression of the hepatitis B virus genome," *Develop. Biol. Standard*(1982) 50:293–300.

Grant Application No. R01AM21344–04 to Rutter, "Differentiation in endocrine and exocrine pancreas" (filing year 1979).

Grant Application No. R01GM21830–05 to Rutter, "Gene expression and replication in eukaryotic organisms" (filing year 1979).

Dialog®Abstract of Japanese Patent No. 58–90517 (May 30, 1983). One page total.

Dialog®Abstract of Japanese Patent No. 64–86971 (Mar. 31, 1989). One page total.

Fraser et al., "Synthesis of chicken ovalbumin in *Saccharomyces cerevisiae*" *Microbiology*(1981) Schlessinger, A.S.M., ed., pp. 392–395.

Maxam et al., "Promoter region for yeast 5S ribosomal RNA" *Nature*(1977) 267:643–645.

Miller, *Experiments in Molecular Genetics*(1972) Cold Spring Harbor Laboratory Press, Cold Spring Harbor, New York. The title page and table of contents are enclosed.

Struhl et al., "High frequency transformation of yeast autonomous replication of hybrid DNA molecules" *Proc. Natl. Acad. Sci. USA*(1979) 76:1035–1039.

Struhl, "Deletion mapping a eukaryotic promoter" *Proc. Natl. Acad. Sci. USA*(1981) 78:4461–4465.

Wu, "Recombinant DNA" *Meth. Enzymol.*(1979) 68 Acadmeic Press, New York.

\* cited by examiner

SYNTHESIS OF HUMAN VIRUS ANTIGENS BY YEAST

CROSS-REFERENCE TO RELATED APPLICATIONS

This application is a continuation of Ser. No. 07/209,504, filed Jun. 21, 1988, which is a divisional of Ser. No. 06/821,146, filed Dec. 12, 1985, now U.S. Pat. No. 4,769,238, which is a continuation-in-part of Ser. No. 06/402,330, filed Jul. 27, 1982, now abandoned, which is a continuation-in-part of Ser. No. 06/289,915, filed Aug. 4, 1981, now abandoned.

BACKGROUND AND PRIOR ART

The present invention relates to the biosynthesis of an antigen of human Hepatitis B virus (HBV) by yeast, brought about by an application of recombinant DNA techniques. Hepatitis B virus is recognized as a major, world-wide public health problem. In addition to the widespread incidence of viral hepatitis, and the persistence of asymptomatic carrier states, Hepatitis B virus has been implicated in the etiology of hepatocellular carcinoma. For a recent review of the molecular biology of Hepatitis B virus, see Tiollais, P., et al., *Science* 213, 406 (1981).

A major effort in current research is to produce a suitable vaccine to provide protective immunity against viral infection. One line of approach to preparing a suitable vaccine has involved attempts to purify the principal antigenic component of the virus, the surface antigen. Hereinafter, the symbol HBsAg is used to identify HBV surface antigen obtained from preparations of intact virus (Dane particles) or purified from the serum of hepatitis carriers. Skelly, J. et al., *Nature* 290, 51 (1981) have reported the purification of water-soluble protein micelles of purified HBsAg. A significant limitation of this approach is that the amount of material which can be prepared depends upon the availability of donors. No technique is known for growing the virus in culture; therefore, in addition to limitations in the amount of source material, there is a risk of contamination of the vaccine with active virus or other components of donor serum, and a possible heterogeneity in the products obtained form various donors.

A second approach has been the attempt to synthesize peptides eliciting antibodies against HBsAg based upon the amino acid sequence of the protein comprising the surface antigen (S-protein) and model studies predicting the most likely antigenic determinants. See, e.g. R. A. Lerner et al., *Proc. Nat. Acad. Sci. USA* 78,3403 (1981). Such work is in a highly preliminary stage, and it may be difficult to assess whether the approach can produce antigens having a practical degree of immunogenicity in a cost-effective manner.

A third approach, employing recombinant DNA techniques, is the synthesis of S-protein, HBsAg or an immunologically reactive equivalent by a microorganism, by endowing a microorganism with genetic capability to produce S-protein, HBsAg or an immunologically reactive equivalent in large amounts, in the absence of other viral gene products. This approach eliminates the possibility of contamination by virus or other viral components and permits large-scale production with economies of scale. Furthermore, it is possible, through appropriate manpulations of the genetic material, to modify the sequence of the protein comprising the vaccine, in order to modify its side effects, or make the vaccine polyvalent. Toward this end, the entire genome of HBV has been cloned in *E. coli* and its entire nucleotide sequence determined (Charnay, P., et al., *Nucl. Acid Res.* 7, 335 (1979); Galibert, F., et al., *Nature* 281, 646 (1979); Valenzuela, P., et al., *Animal Virus Genetics* (B. Fields, R. Jaenisch and C. F. Fox, Eds.) Academic Press, New York, N.Y. (1980), page 57. A single region of the genome was found to code for the S-protein and also for a large pre-sequence of 163 amino acids. The structure of HBsAg is believed to consist of two S-protein chains joined by intermolecular disulfide bonds and held in a prescribed confirmation by additional intra-molecular disulfide bonds. One of the two chains appears to be glycosylated. In the serum of carriers, HBSAG frequently appears in the form of spherical particles with a mean diameter of 22 nm, which are thought to aggregates of the S-protein dimers just described, and possibly contain lipids. In the viral envelope, HBsAg is associated with the lipid-containing viral envelope, which is believed to be derived from membrane components of the host cell.

The antigenicity and immunogenicity of HBsAg depend upon several factors, not all of which are well understood. It has been observed that reduction of the disulfide bonds reduces antigenicity and immunogenicity markedly (Mishiro, S. et al., *J. Immunol.* 124, 1589 (1980)). Therefore, the tertiary configuration contributed by the intramolecular and intermolecular disulfide bonds is thought to contribute to antigenicity and immunogenicity. The contribution of other factors, such as the extent and nature of glycosylation and association with lipid is unclear, although all are thought to contribute to some degree. Aggregation into particles such as the above-mentioned 22 nm particles is thought to contribute significantly to enhancing immunogenicity.

The S-protein has been synthesized in *E. coli* in the form of a fusion protein (Edman, J. C. et al., Nature 291, 503 (1981)). The product included 183 amino acids of pre-beta lactamase, 5–10 glycine residues, and 204 amino acids of S-protein lacking 22 amino acids of the amino terminal end. The fusion protein was immunoprecipitable with anti-HBsAg IgG.

Since it is known that S-protein dimers mishiro et al., supra): and 22 nm particles incorporationg HBsAg (Cabrall, G. A. et al. *J. Gen. Virol.* 38, 339 (1978)) are more antigenic than the associated S-protein, it would be highly desirable to find a biological system capable of producing HBsAg or an immunologically reactive equivalent directly, in substantial quantities.

The steps in converting S-protein to HBsAg or to 22 nm particles are not fully understood, nor is it known to what extent they are host cell-specific. Furthermore, the S-protein gene appears to code for an unusually long pre-sequence of 163 amino acids, whose functional significance, if any, is unknown. In fact it is not known whether the pre-sequence is actually translated in the virus-infected cell. Yeast (*Saccharomyces cerevisiae*) was chosen as a host cell in which to attempt the expression of HBsAg for the following reasons: Yeast is readily grown in culture in large quantities. In fact, the technology of yeast culture on a large scale is well understood. Also, yeast is eucaryotic, so it was hoped that some of the post-translational processing steps which are carried out in a normal host cell might be carried out in yeast. Because of the complex post-translational events that convert S-protein to HBsAg, some of which may be host-cell specific, the nomenclature adopted herein is intended to distinguish different antigenic forms recognized from the work herein disclosed. The unprocessed translation product of the structural gene for surface antigen is termed S-protein. The antigen isolated from plasma of infected donors, from Dane particles or from human hepatoma cell cultures, is termed HBsAg. The expression product of the surface antigen gene in yeast is termed Y-BsAg. The term, immunologically reactive equivalent of HBsAg, is a general term for any immunologically cross-reactive composition comprising S-protein or a portion thereof, of which Y-HBsAg is an example.

Yeast has never previously been used for expression of the genes of a virus which normally multiplies in a different organism. Prior art attempts to express heterologous proteins in yeast have yielded mixed results. An attempt to express rabbit globin, under control of its own promoter, appears to have been unsuccessful in translation of the protein (Beggs, J. D. et al., Nature 283, 835 (1980)). A gene coding for a Drosophila gene has been reported capable of complementing a yeast ade 8 mutant, under conditions of selective pressure for genetic complementation. Isolation of a fuctional protein from the yeast strain was not reported. The gene for human leukocyte interferon has been expressed in yeast, under control of the yeast ADH1 (alcohol dehydrogenase) promoter. In that instance, successful production of an active protein did not require post-translational processing or assembly of components.

DNA transfer vectors suitable for transfer and replication in yeast have been developed (Broach, J. R. et al., Gene 8, 121 (1979); Hartley, J. L. et al., Nature 286, 860 (1980). Most yeast vectors in current use are derived from E. coli vectors, such as pBR322, into which have been inserted a yeast origin of replication. Two types of yeast replication origins are available. The first, derived from a ubiquitous naturally-occurring yeast plasmid, commonly referred to as the 2 micron circle, confers the ability to replicate independently of yeast chromosomal DNA. Another class of vectors contains a replication origin sequence termed ars1 (autonomous replication sequence), derived from the yeast chromosomal replication origin, which also provides autonomous replication capability. Because both bacterial and yeast replication origins are present in the same vector, they can be used in either organism. Selection may be provided for in bacterial systems by the inclusion of antibiotic resistance genes, such as the ampicillin and tetracycline resistance genes of pBR322. Selection in yeast systems typically may be provided for by including a yeast gene complementing a mutation in a suitable auxotrophic host strain. The studies reported herein conveniently utilize yeast vectors containing a promoter isolated from the yeast gene coding for alcohol dehydrogenase (ADH1). (Bennetzen, J. L. et al., J. Biol. Chem. Vol. 257, p. 3018 (1981).

The ADH1 promoter region was isolated from the 5'-flanking region of the yeast ADH1 gene. A fragment containing approximately 1600 base pairs of the ADH1 sequence extending from position −1550 to +17 within the coding region was fused to the yeast CYC1 coding sequence. Studies on transcription of the attached CYC1 coding sequence deomonstrated that transcript starting specificity could be transferred from one yeast gene to another. Smaller fragments, lacking all of the ADH coding region, have subsequentLy been constructed, and shown to be functional in the expression of human interferon. One such fragment, designated 921, is terminated after position −9, and was employed in the present studies.

Because substances reactive with anti-HBsAg antibody exist in several forms, a nomenclature has been adopted herein to distinguish these forms. The translation product of the HBV surface antigen gene is termed the S-protein. S-protein has 226 amino acids whose sequence has been inferred from the nucleotide sequence of its gene and by partial sequence analysis. HBsAg as used herein includes the major surface antigenic component of HBV found in infected patients' serum and in Alexander cells, a hepatocellular carcinoma cell line which synthesizes and excretes 22 nm HBsAg particles (Alexander, J. J. et al., S. Afr. Med. J. 50, 1124 (1976). Both S-protein and HBsAg are antigenic, however, the latter is more reactive against anti-HBV antibody and is considered more immunogenic. Since the structure of HBsAg is not fully characterized, and the contributions to antigenicity and immunogenicity of various modifying steps not fully understood, the term HBsAg is used herein to include any modified form of the S-protein which contributes to its antigenic and immunogenic properties, including, but not limited to, dimerization, glycosylation, and particle assembly.

SUMMARY OF THE INVENTION

The present invention relates to synthesis of HBsAg in yeast. Yeast expression vectors comprising a yeast promoter, ADH1, have been constructed. The region of the HBV genome coding for the S-protein, excluding a possible 163 amino acid presequence, has been transferred to the yeast expression vector.

Using the described yeast vector, the successful synthesis of HBsAg by yeast has been achieved. The product is antigenic (reactive with anti-HBsAg), and a substantial portion is found associated with particles identical in electron microscopic appearance to those found in the serum of HBV-infected patients and in Alexander cells but having a smaller particle size diameter. The HBsAg synthesized by yeast has identical sedimentation behavior to purified, naturally-occurring HBsAq particles purified from Alexander cells as measured by sucrose gradient sedimentation. The present invention demonstrates synthesis and assembly of a higher ordered multi-component structure resulting from expression of a heterologous DNA coding segment in a microorganism.

DETAILED DESCRIPTION OF THE INVENTION

Figure 1:
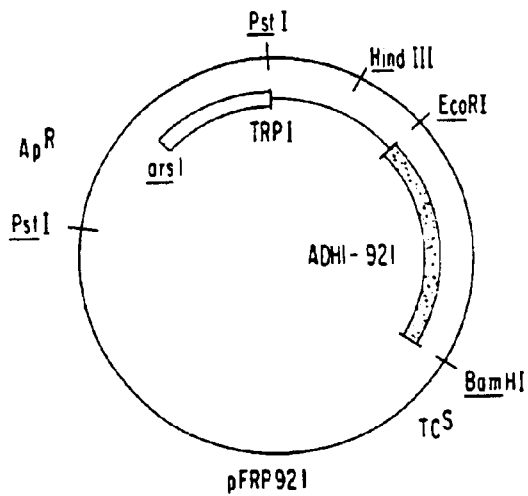
FIG. 1 shows a map for plasmid pFRP-921.

The present invention is believed to be the first instance of biosynthesis and particle assembly of a virus protein in a heterologous host, where the heterologous host (in this instance yeast) is far removed on an evolutionary scale from the normal host (man). The invention was made possible by the development of autonomously replicating DNA transfer vectors for yeast and also by the cloning and characterization of the HBV genome in bacteria. In the present invention, the promoter for the yeast ADH1 gene was used to provide a high level of transcription of the inserted S-protein coding region. In principle, any yeast promoter could be employed instead, preferably an active promoter which provides a high level of transcription. Other suitable active promoters of yeast include those for glyceraldehyde 3-phosphate dehydrogenase, aldolase, pyruvate kinase and phosphoglycerate kinase. It may be that heterologous promoters, such as the HBV S-protein promoter, may also be employed. However, at present, the use of yeast promoters is preferred.

Other proteins of HBV, such as the core antigen, should also be synthesizable by employing the principles and techniques of the present invention. Beyond that, the invention is applicable and will be particularly advantageous in any system where posttranslational processes are desired for making a biologically functional end product, including glycosylation, particle assembly, and possibly specific protein cleavage reactions.

The S-protein gene has three potential points for initiation of translation. The first two are AUG codons located approximately 70 and 90 base pairs from the putative HBV S-protein promoter. The third, which begins the known coding sequence of mature S-protein, is located 522 and 489 base pairs from the first and second, respectively. The third potential start point is therefore much farther away from the HBV S-protein promoter. At present, it is not known which of the AUG codons is the actual starting point for translation. If translation is initiated at either the first or second potential start codons, the transcript either comprises the coding sequence for an unusually long leader of 163 amino acids which must be removed by post-translational processing, or it constitutes an unusual intron which is removed by post-transcriptional processing. If the third AUG is the actual initiation point, then there is an unusually large spacing between the promoter and the start codon.

The data presented herein demonstrate that Y-HBsAg is a particulate, immunologically cross-reactive equivalent of HBsAg which differs from the latter in several ways, although its morphological appearance in the electron microscope is similar to HBsAg. Furthermore, the data demonstrates that Y-HBsAg may be at least as antigenic, per unit weight, as HBsAg, and Y-HBsAg may be at least as effective as HBsAg in eliciting antibody reactive to HBsAg in rodents and in primates.

The rate of expression of the S-protein coding segment may be enhanced by a variety of means. These include modifying the expression vectors to optimize the spacing between the promoter and the start codon of the coding segment, in order to optimize the rate of translation initiation. The addition of a terminator sequence, which directs termination of transcription at a point in the 3' untranslated region following the stop condon of the coding segment, enhances expression, presumably by stabilizing the mRNA transcripts. In the absence of a termination signal, it has been observed that optimizing the length of the 3' untranslated region itself enhanced expression.

The adoption of means to enhance vector stability also increases the yield of the expression product from a culture. Many vectors adapted for cloning in yeast include genetic markers to insure growth of transformed yeast cells under selection pressure, for example, by including a TRP1 gene to permit the growth of a trp1⁻ host in medium lacking tryptophan. Host cell cultures containing such vectors may contain large numbers of untransformed segregants when grown under nonselective conditions, especially when grown to high cell densities. Therefore, it is advantageous to employ expression vectors which do not require growth under selection conditions, in order to Permit growth to high densities and to minimize the proportion of untransformed segregants. Vectors which contain a substantial portion of the naturally occuring two circle plasmid are able to replicate stably with minimal segregation of untransformed cells, even at high cell densities, when transformed into host strains previously lacking two micron circles. Such host strains are termed circle zero (cir⁰) strains. Additionally, the rate of cell growth at low cell densities may be enhanced by incorporating regulatory control over the promoter such that the expression of the S- protein coding region is minimized in dilute cultures such as early to middle log phase, then turned on for maximum expression at high cell densities. Such a control strategy increases the efficiency of cell growth in the fermentation process and further reduces the frequency of segregation of untransformed cells.

In the examples that follow, many of the techniques, reactions and separatin procedures are already well known in the art. All enzymes, unless otherwise stated, are available from one or more commercial sources, such as New England BioLabs, Beverly, Mass.; Collaborative Research, Waltham, Mass.; Miles Laboratories, Elkhart, Ind.; Boehringer Biochemicals Inc., Indianapolis, Ind. and Bethesda Research Laboratory, Rockville, Md., to mention a representative few. Buffers and reaction conditions for restriction enzyme digestion were used according to recommendations supplied by the manufacturer for each enzyme. Partial digestions with restriction enzymes were carried out using a reduced enzyme concentration which was predetermined from preliminary experiments for each enzyme batch. Standard methodology for other enzyme reactions, gel electrophoresis separations and *E. coli* transformation may be found in *Methods in Enzymology*, Vol. 68, Ray Wu, Ed., Academic Press (1979). Transformation of yeast protoplasts was carried out essentially as described by Beggs, (Nature 275, 104–109 (1978).

*E. coli* strains useful for transformation include X1776; K12 strain 294 (ATCC No. 31446); RR1 and HB101. Yeast strains XV610-8c having the genotype (a ade2 ade6 leu2 lys1 trp1 can1) and GM-3C-2, Faye, G. et al., *Proc. Nat. Acad. Sci. USA* 78, 2258 (1981) Genotype: (αLeu2 Trp1 His4 CYC1-1 CYP3-1), were used for yeast transformations. Bacteria were grown and selected according to procedures described by Miller, J. H., *Experiments in Molecular Genetics*, Cold Spring Harbor Laboratory, Cold Spring Harbor, N.Y. (1972). Yeast were grown on the following media: YEPD contained 1% (w/v) yeast extract, 2% (w/v) peptone, and 2% (w/v) glucose; and, in the case of plating media, 3% (w/v) agar. YNB plus CAA cotained 6.7 grams of yeast nitrogen base (Difco Laboratories, Minneapolis, Minn.), 10 mg of adenine, 10 m of uracil, 5 g casamino acids (CAA) (Difco), 20 g glucose; and, in the case of plating media, 30 g agar per liter. Selection for tryptophan prototrophy was made on plates containing 6.7 g yeast nitrogen base (lacking amino acids), and supplemented for all growth requirements of the strain to be transformed except tryptophan.

EXAMPLE 1

Construction of Yeast Vectors

Two yeast vectors have been constructed, one having an ars1 replication origin, the other comprising a 2μ circle replication origin.

The plasmid pFRP-921 has been previously described by Hitzeman et al., Nature 293, 717 (1981). The vector contains the ampicillin and tetracycline resistance genes and replication origin of bacterial plasmid pBR322, the yeast ars1 replicaton origin and trp1 gene together with the ADH1 promoter fragment, designated 921, terminated after position −9 in the nucleotide sequence. A map of pFRP-921 is shown in FIG. 1.

Plasmid pMA56 contained the sequence of bacterial plasmid pBR322, a yeast trp1 gene for selection in yeast, the yeast 2μ circle replication origin, and an ADH1 promoter fragment designated 906, terminated after nucleotide −15 at the 3'-end. Steps and construction of pMA56 are outlined as follows and diagrammed in FIG. 2.

Figure 2:
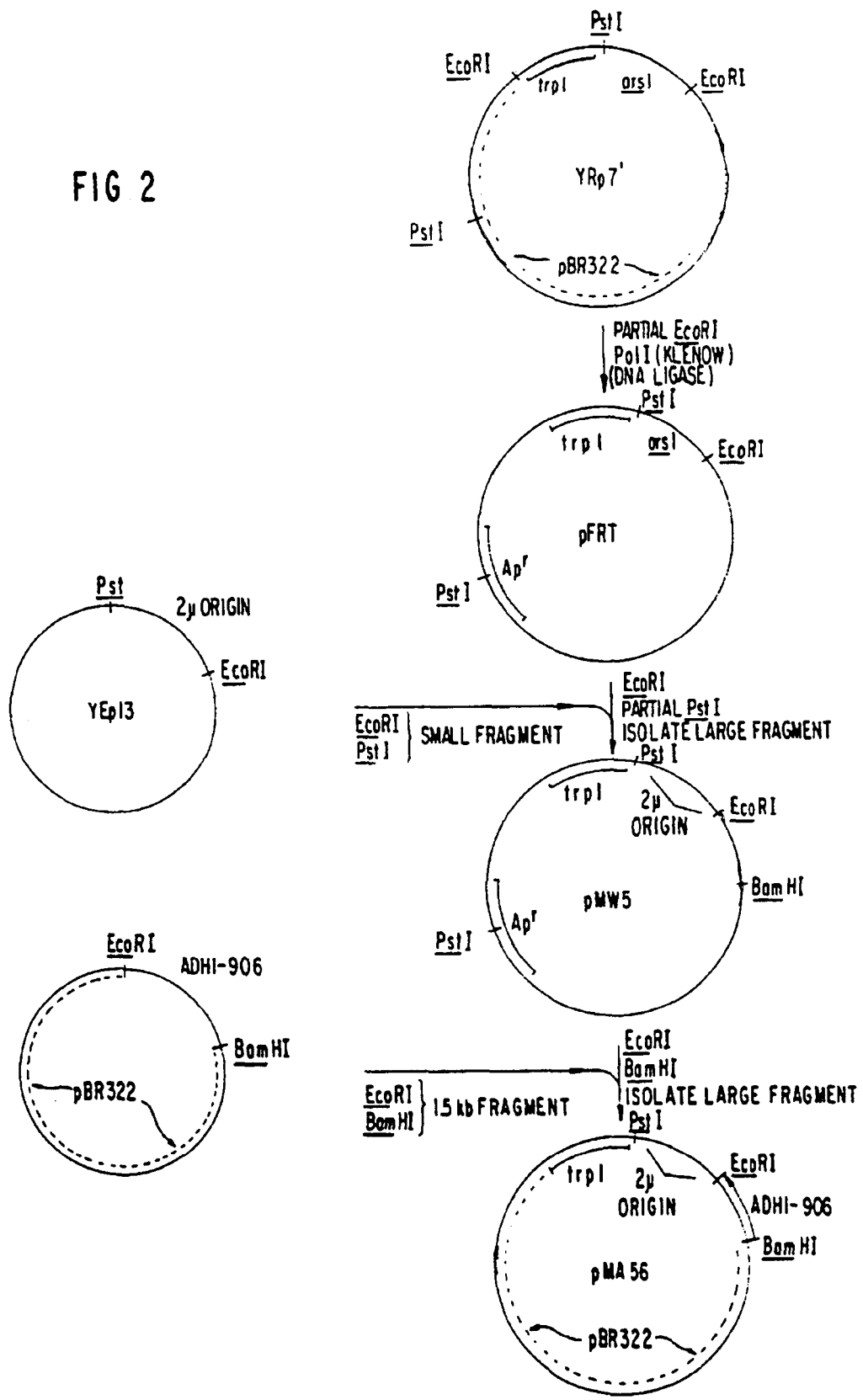
FIG. 2 shows the construction of plasmid pMA56.

Plasmid YRp7' (Stinchcomb, D. T. et al., Nature 282, 39 (1979)) containing the yeast trp1 and ars1 sequences inserted at the EcoRI site o pBR322 was used as starting material. As a result of inserting the yeast sequences, the plasmid contained two EcoRI sites (FIG. 2). One of these was deletes by partial digestion with EcoRI endonuclease, to digest, on the average, only one of the two sites per molecule. The resulting unpaired ends of the linear molecules were filled in by the reaction catalyzed by DNA polymerase I (Klenow fragment), and the resulting blunt ends were rejoined in a DNA ligasecatalyzed reaction to re-establish a closed circular DNA molecule. One of the resulting plasmids, designated pFRT, was chosen since it had retained the EcoRI site adjacent to the ars1 region.

As shown in FIG. 2, the ars1 replication origin was bounded by a PstI site and an EcoRI site. At the same time, the plasmid YEp13 (Broach et al., supra) contained the 2μ circle replicaton origin similarly bounded by a PstI site and an EcoRI site. Therefore, cleavage of pFRT and YEp13 by PstI and EcoRI endonucleases yielded, respectively, a large linear fragment lacking a yeast replication origin from pFRT and a small DNA fragment comprising the 2μ circle replication origin from YEp13. Plasmid pFRT was digested with PstI endonuclease under partial digestion conditions to reduce the frequency of cleavage at the PstI site within the ampicillin-resistance gene. The desired fragments were purified by preparative gel electrophoresis, mixed together and covalently joined in a DNA ligase-catalyzed reaction. The resulting plasmid, designated pMW5, was selected for ability to confer ampicillin resistance.

The ADH1 fragment 906 was inserted into pBR322 between the BamHI and EcoRI sites. The promoter fragment was released by digestion with BamHI and EcoRI endonucleases. A fragment of 1.5 kilobases (kb), the ADH1-906 fragment, was isolated by preparative gel electrophoresis. Plasmid MW5 was simiarly digested with EcoRI and BamHI endonucleases. The large fragment, having an EcoRI-specific end and a BamHI-specific end, was isolated by preparative gel electrophoresis, mixed with the ADH1-906 fragment, and covalently joined by a DNA ligase-catalyzed reaction. The resulting plasmid, designated pMA56 and diagrammed in FIG. 2, was selected by ampicillin resistance in E. coli.

Plasmids pFRP-921 and pMA56 are structurally similar, differing primarily in having an ars1 replication origin (pFRP-921) or a 2μ circle replication origin (pMA56), respectively. In addition, the ADH1 promoter fragments differ slightly, as described. Both are similar in having bacterial replication origins and selection markers for growth in E. coli. Both contain a yeast TRP1 gene to permit selection in yeast trp1 host strains.

EXAMPLE 2

Construction of a Yeast Plasmid Containing the S-protein Coding Region

Analysis of the nucleotide sequence of HBV DNA reported by Valenzuela, P. et al. in Animal Virus Genetics, Academic Press, New York, N.Y (1980), pp. 57–70, showed the location of the S-protein coding region. The region is contained within the TacI-HpaI fragment of 835 base pairs length. This fragment includes 26 base pairs preceding the AUG codon for the N-terminal methionine of the S-protein. (Most of the region coding for the putative presequence described supra, as well as the first two AUG codons, are missing from the TacI-HpaI fragment). The fragment also contains the entire S-protein coding region (678 bp), a TAA stop codon, and 128 bp following the stop codon.

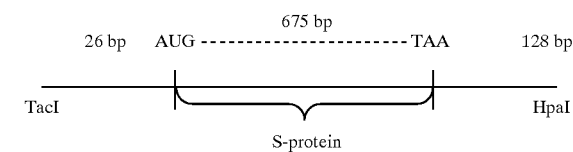

Approximately 500 μg of DNA from plasmid pHBV-3300 (Valenzuela, P. et al., Nature 280, 815 (1969)) were digested to completion with a combination of the restriction enzymes EcoRI and HpaI. Approximately 60 μg of the fragment EcoRI-HpaI of 965 base pairs were isolated by preparative gel electrophoresis in agarose. This fragment was then digested to completion with the restriction enzyme TacI. Approximately 30 μg of the 835 base pair TacI-HpaI fragment were isolated by Preparative gel electrophosresis in agarose.

The 835 bp fragment was treated to provide EcoRI specific ends by addition of EcoRI linker oligonucleotides (obtained commercially from Collaborative Research, Waltham, Mass.). The linker oligonucleotides were joined to approximately 3–5 μg of the fragment by blunt-end ligation catalyzed by T4 DNA ligase. The fragment was then digested with EcoRI endonuclease to cleave unreacted and self-ligated linkers and to produce EcoRI-specific unpaired ("sticky") ends.

Plasmid pFRP-921 was digested with EcoRI endonuclease and treated with alkaline phosphatase to prevent self-ligation (Shine, J., U.S. Pat. No. 4,264,731). A mixture of the TacI-HpaI fragment with EcoRi ends and EcoRI-digested pFRP-921 was incubated with DNA ligase to form covalently closed circular DNA having the S-protein coding fragment inserted in the yeast vector. The resulting plasmids were used to transform E. coli, selecting for ampicillin resistance. Both possible orientations of the S-protein coding sequence with respect to the yeast promoter were isolated and characterized by the cleavage products resulting from treatment with a restriction enzyme acting on an asymmetrically located site within the HBV insert. Plasmids pHBS-11 (in correct orientation) and pHBS-12 (opposite orientation) were selected and amplified in E. coli.

The foregoing procedure was employed as described, using pMA56 instead of pFRP921 for inserting the TacI-HpaI S-protein coding fragment into pMA56 at the EcoRI site. Two plasmids were isolated and characterized, pHBS-16 containing the viral gene in the correct orientation with respect to the ADH1 promoter, and pHBS-20 having the S-protein gene in the opposite orientation.

EXAMPLE 3

Synthesis of HBsAg in Yeast

Protoplasts of the yeast-recipient strain XV610-8C or GM3 C-2, were separately incubated with DNA from each of the four plasmids, pHBS-11, pHBS-12, pHBS-16 and pHBS-20, under the transformation conditions described, and plated on agar plates in medium lacking tryptophan.

Surviving colonies, transformed to tryptophan prototrophy, were isolated. To test for HBsAg synthesis, yeast strains tranformed with each of the four plasmids were separately grown in liquid cultures, in medium lacking tryptophan, and harvested in mid-log phase. The cells were collected by centrifugation, and cell extracts were prepared by grinding the cells with glass beads in a buffer of 0.01M sodium phosphate (pH 7.4) containing 0.01M beta-mercaptoethanol, and 0.1% (v/v) NP-40 detergent [polyoxyethylene(9) octaphenol]. The presence of HBV surface antigen was assayed using a radioimmunoassay kit commercially available from Abbot Laboratories, North Chicago, Ill. Qualitatively, the plasmids containing the surface antigen coding fragment in correct orientation, pHBS-11 and pHBS-16, produced readily detectible amounts of surface antigen, whereas no detectible surface antigen was found in extracts of cells transformed with pHBS-12 or pHBS-20. Quantitatively, a 200 ml culture of XV-610-8C containing pHBS-16 produced 1–2 μg of surface antigen protein. Cells containing pHBS-11 produced ½ to ⅓ as much surface antigen, possibly attributable to a lower copy number per cell of plasmids having the ars1 replication origin.

All cell extracts were analyzed by sucrose gradient sedimentation. Pre-formed 5% (w/v) to 30% (w/v) sucrose gradients were layered with an extract of XV6100 -8C/pHBS-16 cells prepared as described, and control gradients were layered with a preparation of HBsAg purified from an Alexander cell culture. The gradients were centrifuged in a swinging bucket rotor for 8 hours at 27,000 rpm. After centrifugation, fractions were collected and assayed by the above-described radioimmunoassay. Surprisingly, HBsAg synthesized by yeast was found to have exactly the same sedimentation properties as HBsAg isolated from Alexander cells. A sedimentation value of approximately 60S was calculated for both HBsAg preparations.

HBsAg synthesized by yeast was purified by a combination of equilibrium centrifugation in cesium chloride and sedimentation in a sucrose gradient. 100 Ml of cells grown to an O.D. of 2.0 at 650 nm were harvested by centrifugation to yield 0.150 ml packed cells. The cell extracts were prepared by grinding the cells with glass beads (as described above) such that, after centrifugation at 6,000 rpm for 15 minutes to remove cell debris, a total volume of 0.5 ml of extract resulted. The extract contained about 30 mg/ml protein and a total of about 1 μg HBsAg. The extract was layered on a discontinuous cesium chloride gradient from 1.1 g/cm$^3$ to 1.4 g/cm$^3$, and centrifuged in a swinging bucket rotor (SW41, Beckman Instruments, Fullerton, Calif.) at 30,000 rpm for 24 hours. After centrifugation, fractions were collected and assayed as before. A control tube containing Alexander cell HBsAg was identically treated, as a marker. Yeast HBsAg comigrated with the Alexander cell HBsAg peak, with a bouyant density of 1.19 g/cm$^3$. Fractions containing yeast HBsAq were pooled, dialyzed and loaded on a 5–30% (w/v) preformed sucrose gradient, and centrifuged at 30,000 rpm for 36 hours. Again, as previously observed, the peak of yeast HBsAg coincided exactly with HBsAg from Alexander cells. Pooled peak fractions had a total protein concentration of 0.01 mg/ml and an overall yield of HBsAg of 15%.

Figure 3:
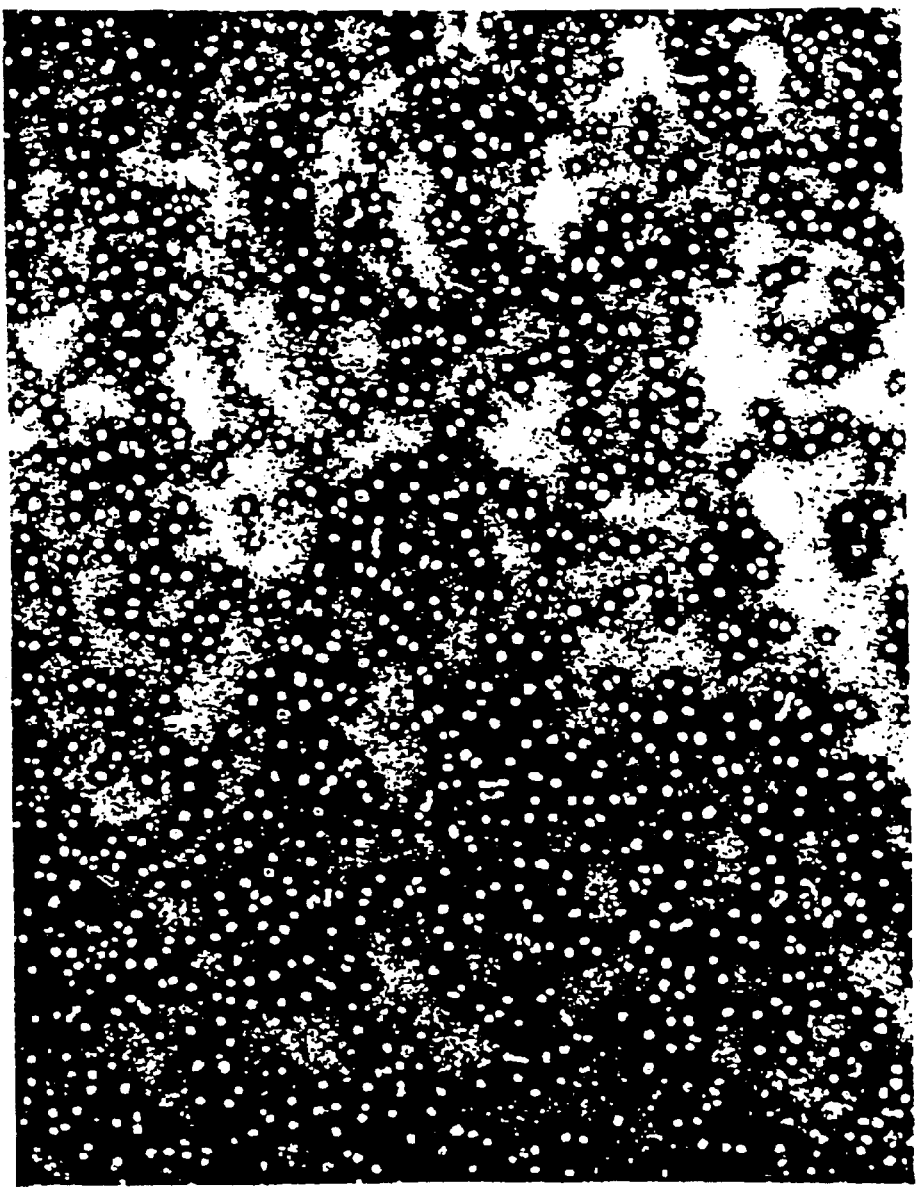
FIG. 3 shows a half-tone reproduction of an electron micrograph of particles of HBsAg synthesized in yeast.

From the sedimentation data, it was apparent that HBsAg was synthesized in yeast in the form of particles or aggregates. The nature of these particles was further characterized by electron microscopy. HBsAg particles synthesized from yeast and purified as described were adsorbed onto carbon film grids and stained with uranyl acetate stain (2% (w/v) for 7 minutes). Under the electron microscope, particles of HBSAG synthesized in yeast were observed, had an identical appearance but smaller diameter compared with HBsAg from Alexander cells. In these studies Alexander cell HBsAg particles had a diameter of about 20 nm, whereas Y-HBsAg particle diameter was from about 16 to about 17 nm (see FIG. 3). These results are believed to be the first demonstration of assembly into a higher order structure of a heterologous protein in a microorganism host.

Higher yields, up to five-fold, have been obtained using as host the yeast strain GM3C-2. The strain is a petite strain whose increased dependence upon carbohydrate metabolism may result in a higher activity for the ADH promoter. The high expression level observed in GM-3C-2 may also be the result of using a modified vector, pHBS-25, containing the S-protein coding fragment flanked by an ADH1 promoter fragment and an ADH termination fragment. The Tac1-HpaI HBV coding segment was fitted with HindIII oligonuclectide linkers and joined at the 5'-end to the ADH1 promoter fragment ADH1-906 terminated in a HindIII linker sequence at its 3' end. The 3'-end of the HBV segment was joined to a 450 bp HindIII-BamHI fragment of the ADH1 gene containing the coding region for the 43 C-terminal amino acids of ADH, the stop codon TAA and part of the 3' untranslated region (see Bennetzen et al., J. Biol. Chem., Vol. 257, p. 3018 (1982), such that both fragments were oriented in the same direction of transcription. The resulting composite segment, ADH-H-5-S-protein-ADH-terminator, was flanked by BamHI sites, permitting insertion at the BamHI site of pMA56. When inserted such that the ADH terminator section was adjacent to the ADH1-906 promoter fragment, the resulting vector was designated pHBS-25.

The construction of vectors of the 25 series analagous to pHBS56-3 and pHBS56-5 (Example 6) is readily accomplished using the composite genes for S-protein flanked by the ADH promoter and terminator segments described in Example 6. The composite gene derived from pHBS16-3 is inserted at the Sph1 site of pMA56, linearized by Sph1 digestion and treated with alkaline phosphatase to prevent reconstitution of pMA56 in the absence of the inserted composite gene, as described by Shine, U.S. Pat. No. 4,264,371. In this construction, pHBS25-3 and pHBS25-5 differ from pHBS25 in that the composite gene is inserted at the Sph1 site of pMA56 rather than the nearby BamMI site of pMA56.

The transfer vector pHBS-16 and a yeast strain comprising the strain XV610-8C transformed by plasmid pHBS-16 have been placed on deposit in the American Type Culture Collection, 12301 Parklawn Drive, Rockville, Md.

EXAMPLE 4

This example demonstrates removal of a 5'-untranslated segment of HBV-DNA. The DNA segment comprising the S-protein region isolated as described in Example 2 included an untranslated 26 base pair segment at the 5'-end of the coding region, lying between the promoter and the ATG start codon. The following procedure was developed to remove all, or all but one, of the bases of the 5'-untranslated region of the HBV-DNA preceding the S-protein coding region.

The plasmid pHBS-5 was digested with EcoR1 endonuclease generating a fragment of approximately 850 base pairs including the S-protein coding region and flanking 3'-and 5'-untranslated regions, terminated by EcoR1 linker oligonucleotide segments. The HBV-DNA segment was reisolated by preparative gel electrophoresis, electroeluted and divided into samples which were digested with the exonuclease Bal-31 for varying times from 0.5 to 30 minutes at 37° C. The extent of exonuclease digestion was characterized qualitatively by digesting a portion of each sample with XbaI endonuclease. The S-protein coding region contains an XbaI site beginning 92 base pairs from the first base of the start condon. Therefore, samples in which Bal-31 digestion had proceeded beyond the XbaI site would yield only one fragment upon gel electrophoresis after XbaI endonuclease incubation while samples with fewer bases removed would yield two classes of fragment: a homogeneous large fragment and a heterogeneously sized small fragment. Samples yielding only one XbaI fragment were discarded. Samples yielding two size classes of fragments were blunt-ended by incubation with DNA polymerase I (Klenow fragment, see Klenow, H., et al., Proc. Nat. Acad. Sci. 65, 168 (1970) in the presence of all four deoxynucleotide triphosphates. Linker oligonucleotides containing the EcoR1 recognition site were added by blunt-end ligation using T4 DNA ligase. EcoR1 specific cohesive ends were generated by digestion with EcoR1 endonuclease. The modified DNA was isolated by gel electrophoresis, electroeluted and joined to EcoR1-digested, alkaline phosphatase treated pBR322, in a DNA ligase catalyzed reaction. The recombinant plasmids were then used to transform *E. coli* HB-101.

Two strategies were employed for screening and characterizing clones with shortened 5'-untranslated segments. In the first, individual colonies were screened for the presence of S-protein coding region by in situ colony hybridization using labeled S-protein coding DNA as a probe. Colonies screening positively for the presence of the S-protein coding region were used to start cultures from which vector DNA was prepared. The vector DNA was incubated by EcoR1 endonuclease to excise the S-protein coding region. The S-protein coding DNA thus prepared was analyzed either by determining the size of fragments generated by Xba1 endonuclease digestion or by DNA sequence analysis of the 5'-terminal sequences (Maxam, A., et al., Proc. Nat. Acad. Sci. USA 74, 560 (1977)).

A second screening strategy was used to detect clones in which the 5-untransalted region had been completely removed or terminated one base short of the start codon. The method exploited the observation that the first four bases of the S-protein coding sequence, ATGG, when joined to an EcoR1 linker oligonucleotide (GGAATTCC) generated a recognition site for the restriction endoculease NcoI: CCATGG. The NcoI site thus generated would be unique in the vector, since neither pBR322 nor the S-protein coding region contains an NcoI site. Therefore, any S-protein coding segment in which the Bal-31 digestion was terminated precisely at the ATG start codon would be characterized by the generation of a new NcoI site when joined to an EcoR1 linker oligonucleotide. As it happens, in HBV-DNA there is a C residue adjacent to the ATG start codon of the S-protein region, in the 5'-untranslated region. Therefore, Bal-31 digests that retain only the last C of the 5'-untranslated region will also generate an NcoI recognition site when jointed to an EcoR1 linker oligonucleotide. These two specific constructions were screened for by incubating the clones with a combination of NcoI and XbaI endonucleases followed by gel electrophoresis of the fragments generated, if any. Those clones yielding a 96 base pair fragment were therefore selected, as these had all or all but one of the 5'-untranslated base removed, but retained the ATG start codon. The exact sequence was then confirmed by DNA sequence analysis using the Maxam et al. procedure. The resulting plasmid, combining pBR322 with a modified HBV segment with the entire 5'-untranslated region of the S-protein gene deleted, inserted at the EcoR1 site, was designated pHBS5-3. (See FIG. 4). The HBV-DNA segment in pHBS5-3 was also incidentally modified by the removal of about 40 base pairs of the 3' untranslated region, due to concomitant action of Bal-31 exonuclease at the 3' end.

Expression vector construction analogous to pHBS16, described in Example 2, was carried out by insertion of the modified HBV-DNA segment of pHBS5-3 in place of the corresponding segment in pHBS16. For this purpose, a "16-type" vector was prepared by EcoR1 endonuclease digestion and religation, followed by selection for a vector in which the HBV-DNA was deleted. Expression vectors constructed by the insertion of modified HBV-DNA segments at the EcoR1 site of the 16-type vector were characterized by the designation. pHBS16-X, where X is a number characterizing the modification of HBV-DNA inserted at the EcoR1 site. Thus, the HBV-DNA segment transferred from pHBS5-3 to the 16 vector generated an expression plasmid designated phHBS16-3. (See FIG. 4). All constructions were screened for correct orientation of the S-protein coding region with respect to the ADH1 promoter by combined digestion with BamHI and XbaI endonuclease digestion. Correct orientation yielded a Bam- Xba fragment approximately 1600 base pairs in length whereas incorrect orientation yielded a longer fragment.

The host strain for the 16 series expression vectors was *Saccharomyces cerevisiae AB* 35-D3-D a, leu2-3, leu2-112, ura3-52, trp1-289, his4-580, ade2 or *Saccharomyces cerevisiae* AB 35-14-D. Sample cultures of the host strain transformed with either pHBS16 or pHBS16-3 were grown under equivalent conditions and Y-HBsAg was qualitatively assayed by radioimmune assay as described in Example 3. Cells transformed with pHBS16-3 produced approximately 2.2 times as much Y-HBsAg per cell as those transformed by pHBS16.

EXAMPLE 5

A further modification was made of the vector construction described in Example 4, in which the 3'-untranslated region removed during the Bal-31 digestion was restored. The strategy of this construction was to combine, at the XbaI site internal to the S-protein coding region, a fragment of the coding region derived from pHBS5-3, modified as described in Example 4, together with an unmodified fragment from pHBS5 having an intact 3'-untranslated region.

The HBV-DNA segment of pHBS5 containing the 5'-untranslated region and promoter proximal part of the S-protein coding region was removed by the sequential action of ClaI endonuclease and XbaI endonuclease. The plasmid was first cleaved with ClaI endonuclease. The resulting unpaired ends were filled in using DNA polymerase I Klenow fragment in the presence of the four deoxynucleotide triphosphates to provide a linear vector with blunt ends. The DNA was then digested with XbaI endonuclease and alkaline phosphatase. The latter treatment was intended to insure that the ends generated by the foregoing series of steps could not rejoin to one another in the presence of DNA ligase, (Shine, J., supra).

The modified HBV-DNA of pHBS5-3 containing the promoter proximal portion of the coding region for S-protein was also prepared by sequetial endonuclease digestion. Plasmid pHBS5-3 was first cleaved with EcoR1 endonuclease and blunt ended with DNA polymerase I Klenow fragment in the presence of the four deoxynucleotide triphosphates. The DNA was then cleaved with Xba endonuclease. The small fragment resulting from XbaI cleavage, approximately 100 base pairs having a blunt EcoR1 end and an XbaI end was isolated by gel electrophoresis and electroelution. The purpose of sequential endonuclease treatment in both instances was to insure that the 100 base pair fragment would be joined in correct orientation with the cleaved vector DNA. The 100 base pair fragment derived from pHBS5-3 was mixed with modified vector DNA derived from PHBS5, in the presence of DNA ligase under conditions permitting blunt end ligation as well as the joining of paired ends derived from the XbaI cuts. Transformants were selected and identifed by the existence of an Nco1 site, derived from the small fragment from pHBS5-3 (See Example 4).

It was anticipated that the EcoR1 site adjacent to the Nco1 site would be regenerated by the construction strategy employed. However, one base pair in the filled in EcoR1 site was not regenerated by the DNA polymerase treatment. Consequently, the EcoR1 site was not regenerated as expected. Fortuitously however, the rejoined sequences did regenerate the ClaI site.

Figure 4:
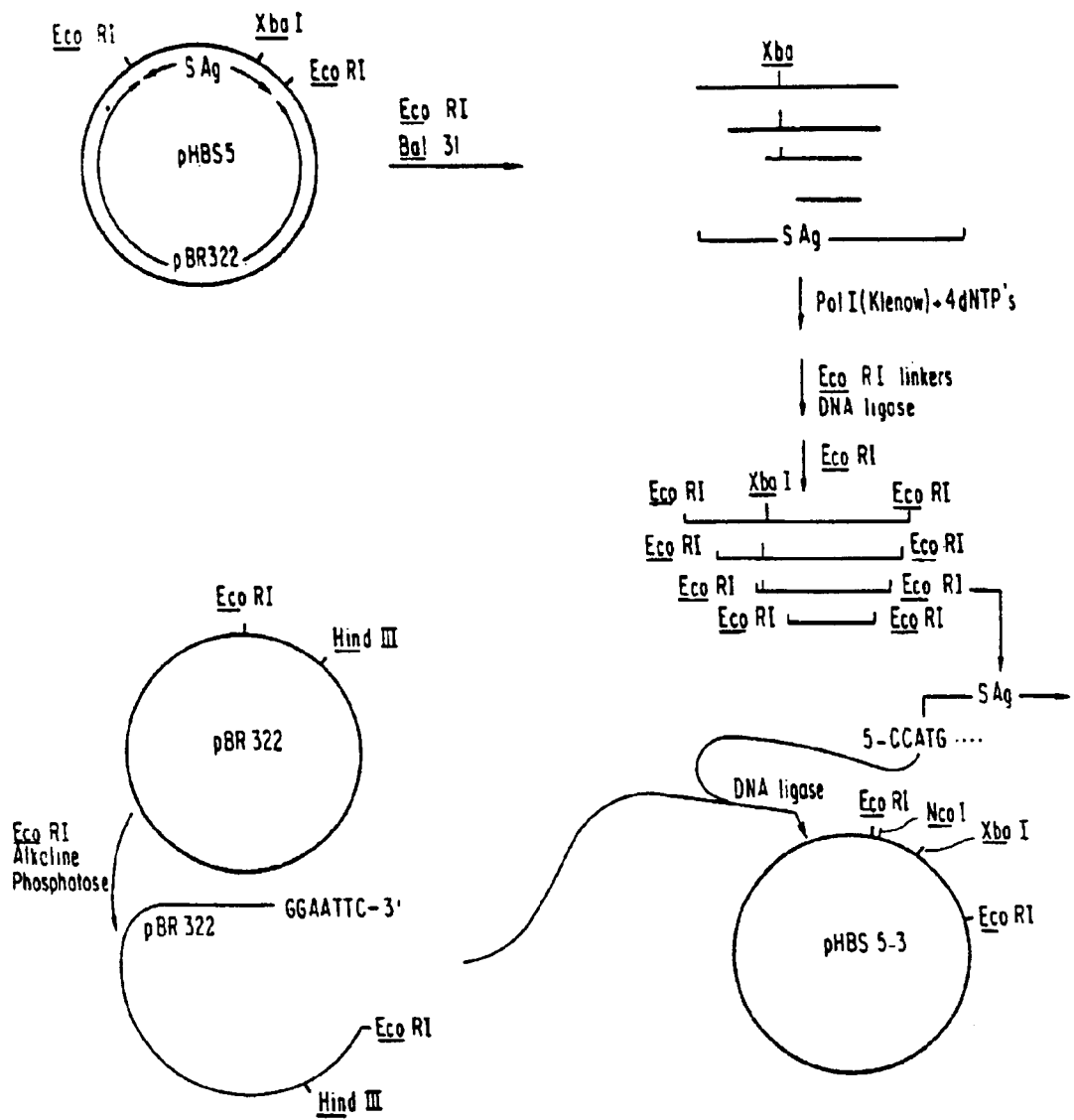
FIG. 4 shows the construction of plasmid pHBS 5-3.
Figure 5:
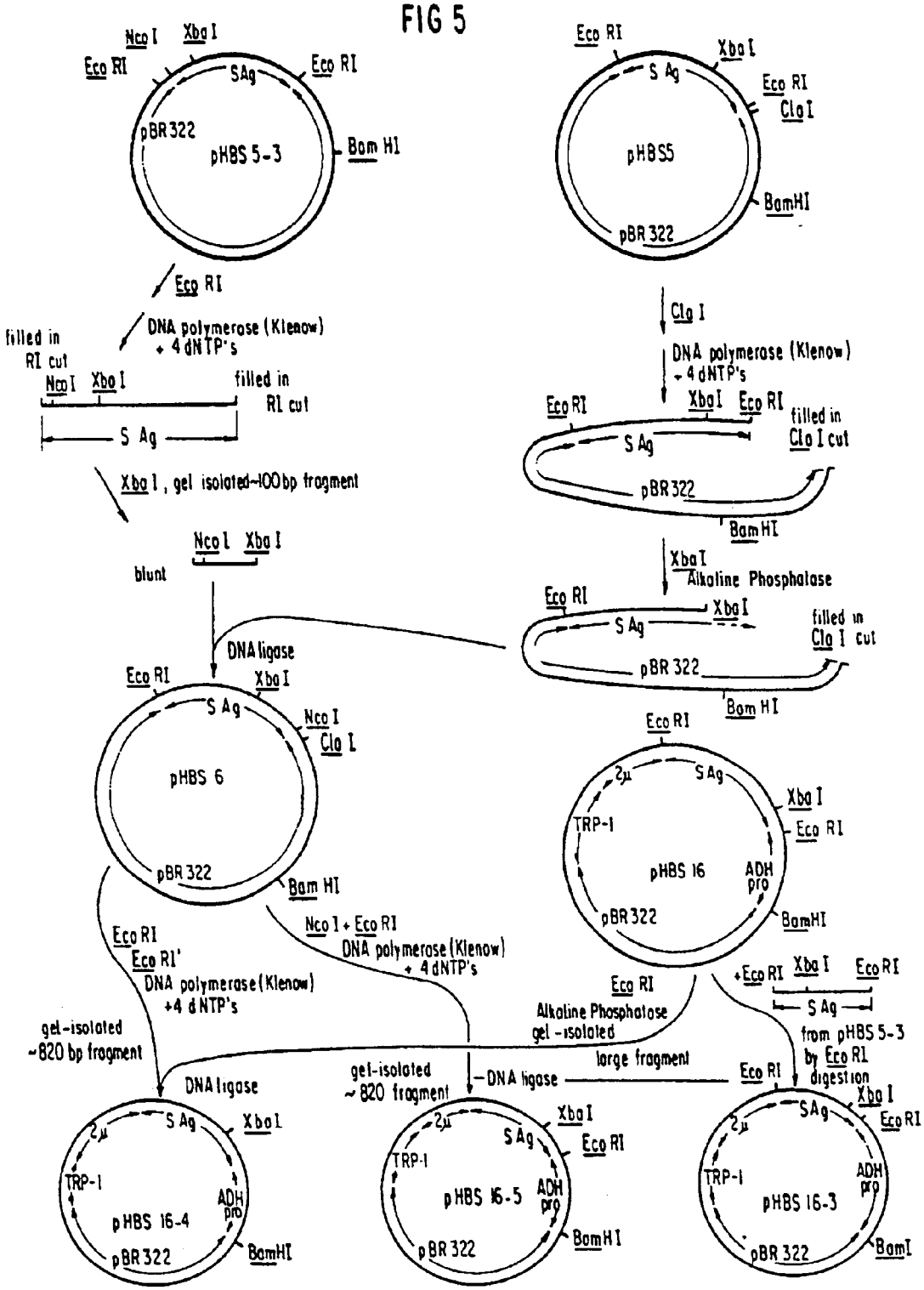
FIG. 5 shows the construction of plasmids pHBS 16-4, pHBS 16-5, and pHBS 16-3.

DNA nucleotide sequence analysis of the resulting vector, designated pHBS6, diagrammed in FIG. 4, confirmed that the HBV-DNA region of the vector contained the entire S-protein coding region and 3' untranslated region together with a deletion of the 5' untranslated region as decribed for pHBS5-3. The HBV-DNA segment modified as in pHBS6 was transfered to an expression vector of the 16 series as follows: The HBV-DNA region of pHBS6 was isolated by combined action of NcoI and EcoR1 endonucleases and blunt ended by incubation with DNA polymerase I Klenow fragment in the presence of the four deoxynucleotide triphosphates. The resulting 820 base pair fragment was isolated by gel electrophoresis and electroelution. The expression vector pHBS16, or the "16-vector" described in Example 4, was cleaved by EcoR1 endonuclease action, blunt ended using DNA polymerase 1 Klenow fragment in the presence of the four deoxynucleotide tri-phosphates, and treated with alkaline phosphatase. The HBV-DNA fragment was then joined to the treated 16 vector by blunt end ligation using T4 DNA ligase. Correct orientation of the fragments regenerated an EcoR1 site between the ADH promoter and the start codon of the S-protein coding region. DNA nucleotide sequence analysis was carried out confirming the structure of the resulting construction, designated pHBS16-5, diagrammed in FIG. 5.

The relative rate of expression of Y-HBsAg for yeast cells transformed by pHBS16-5 was measured under the same conditions as for pHBS16-3, described in Example 4. Expression of Y-HBsAg by *Saccharomyces cerevisiae* AB-35-D3-D transformed by pHBS16-5 was approximately 2.8 times greater per cell as measured by radioimmumo assay, than expression by cells transformed with pHBS16.

A related construction using the HBV-DNA segment of pHBS6 was carried out using an identical procedure with the exception that the HBV-DNA fragment was excised by an EcoR1 endonuclease preparation having some EcoR1* activity. After ligation with the 16 vector, prepared as previously described, the expression vector was found to have lost the EcoR1 site as well as the NcoI site adjacent to the ATG start codon of the S-protein coding region. The resulting expression plasmid was designated pHBS16-4. The nucleotide sequence adjacent to the S-protein start codon was 5' . . . ACTATCTGGCATGG . . . 3'. The rate of expression in yeast cells transformed with pHBS16-4 was comparable to that of pHBS16-5 transformed cells, within experimental error. The structure of pHBS16-4 is diagrammed in FIG. 5.

The nucleotide sequence adjacent to the S-protein start codon of PHBS-16-3 was 5' . . . ACTATCTGGAATTC-CCATGG . . . 3'. The sequence for pHBS-16-5 was 5' . . . ACTATCTGGAATTCATGG . . . 3'. The sequence difference between 16-3 and 16-5 was a consequence of blunt-ending the DNA after EcoR1 digestion of pHBS-6.

EXAMPLE 6

This example describes details of the construction of a series of vectors for expression characterized by having the entire two micron circle plasmid DNA sequence within their sequence together with DNA segments comprising the promoter and transcription terminator sequences of the yeast ADH gene, with the S-protein coding region sandwiched between the ADH promoter and the ADH terminator regions. These vectors were designated "56" series vectors and their nomenclature is consistent with the nomenclature of the 16 series of expression vectors. Thus, the expression vector pHBS16-3 contains the S-protein gene modified as described for pHBS16-3, while pHBS56-5 contains HBV-DNA modified as described for pHBS16-5, as described in Examples 4 and 5 respectively. The full length two micron circle DNA provides for stable replication in a circle zero host strain in the absence of metabolic selection pressure. The ADH terminator was provided to enhance the stability of S-protein mRNA transcripts.

The parent plasmid for the construction of 56 type vectors was pCl/1 which was a hybrid plasmid between pBR-322 and a two micron circle plasmid joined at their EcoR1 sites. The two micron circle portion was previously modified to contain an inserted LEU2 gene of yeast and obtained from the plasmid pJrBD219 described by Beggs, J. et al., Nature 275, 104 (1978). The restriction map of pCl/1 is shown in FIG. 6.

Figure 6:
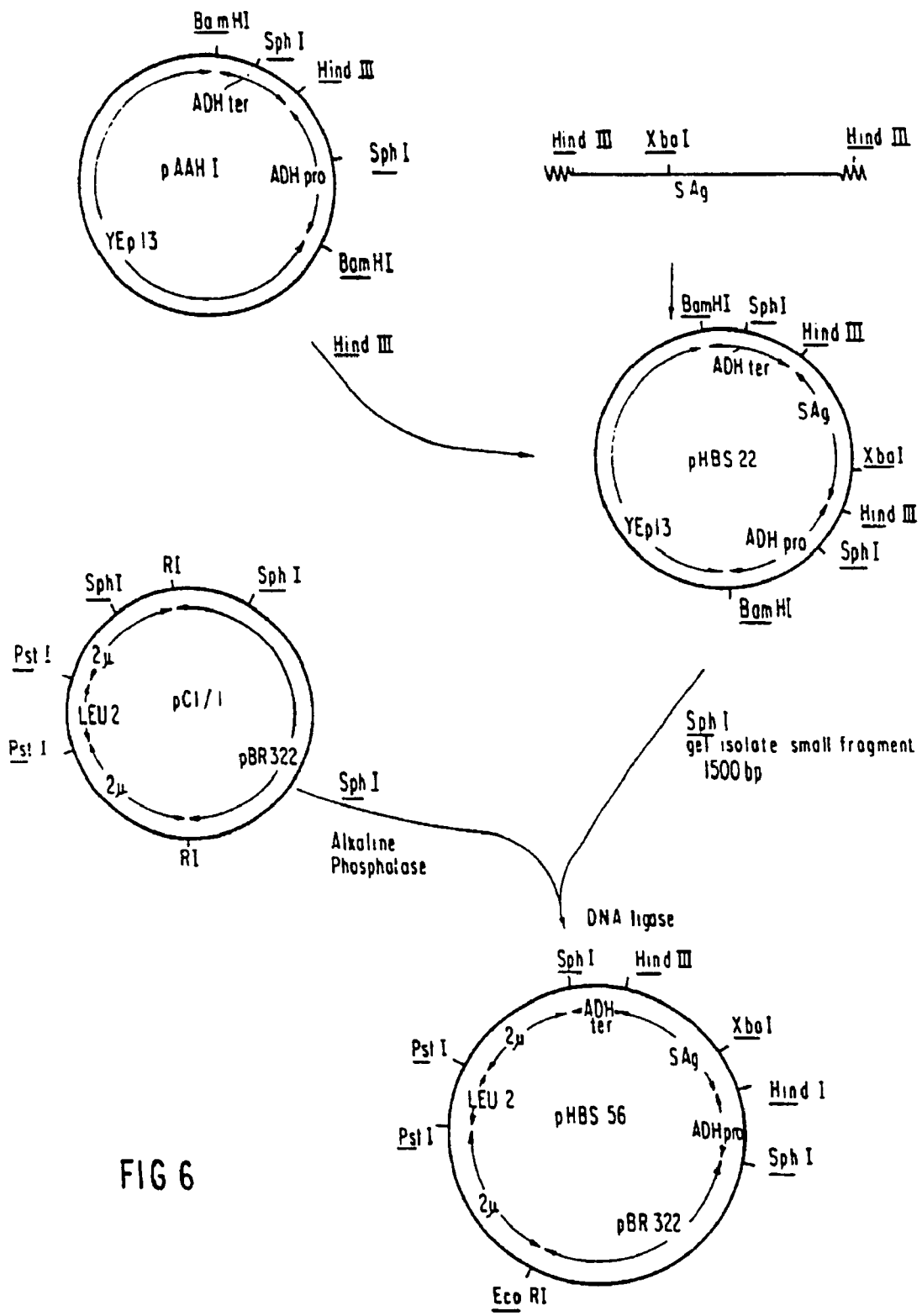
FIG. 6 shows the construction of plasmid pHBS 56.

It can be seen from FIG. 6 that digestion of pCl/1 with endonuclease Sph1 deleted a portion of the plasmid spanning the two micron-pBR-322 joint. It was observed that the active portion of the ADH1 promoter region was contained within an Sph1 HindIII fragment of approximately 300 base pairs length (See sequence of the ADH1 gne, by Bennetzen, J. L. and Hall, B. D., J. Biol. Chem. 257, 301 (1982)). The recognition sequence for Sph1 is GCATGC and such a sequence exists in the ADH promoter beginning at position −413. Similarly, the yeast terminator sequence was contained within a HindIII Sph1 fragment of about 330 base pairs. In both cases the Sph1 site was distal to the coding region so that the HBV S-protein coding region could be inserted between them if provided with HindIII sites at its termini. The precursor source for the ADH promoter and terminator segments was plasmid PAAH5 containing a 1500 base pair ADH1 promoter fragment terminated at position $-9$ in the nucleotide sequence (Hitzeman, R. A. et al., supra, and an approximately 450 base pair terminator unit from nucleotides 913 to 1368 in the ADH bene nucleotide sequence, joined by a HindIII site between the fragments and cloned into the BamH1 site of the vector YEp13, (Broach, J. and Hicks, J., Gene 8, 121 (1979)). The HBV-DNA segment of pHBS5 was excised hy EcoR1 digestion. The protruding ends were filled in using DNA polymerase I Klenow fragment and joined at both ends with HindIII linker oligonucleotides having the sequence CAAGCTTG. After HindIII endonuclease digestion to expose unpaired, HindIII specific ends on the HBV-DNA segment, the segment was joined to HindIII cut plasmid pAAH5, thereby placing the HBV S-protein coding sequence between the ADH promoter and terminator fragments. A plasmid with the S-protein gene in correct orientation with respect to the promoter and terminator fragments, as determined by restriction analysis, was designated pHBS-22. The ADH promoter and terminator sequences were each found to contain an SphI site (recognition sequence GCATGC) making it possible to excise the entire composite gene comprising about 400 base pairs of ADH1 promoter, HBV S-protein region and about 330 base pairs of ADH1 terminator by digestion with SphI endonuclease. Digestion of pHBS22 with SphI endonuclease yielded the intact composite gene in a fragment of approximately 1500 base pairs. The fragment was joined with SphI-cut vector pCl/1. E. coli. HB101 transformants were screened for ampicillin resistance and sensitivity to tetracycline, since the segment excised by SphI endonuclease digestion of pCl/1 deleted a portion of the tetracycline resistance gene of the pBR322 segment. The structure of the resulting vector, designated pHBS56 was further confirmed by restriction analysis. E. coli. HB101 transformants obtained from the products of the ligase reaction were cloned on plates containing ampicillin. Plasmid DNA from single colony isolates grown in culture was screened by restriction endonuclease analysis for the insertion and correct orientation of the S-protein coding region. The plasmid selected, pHBS-56 containing the HBV S-protein coding region in correct orientation with respect to the ADH promoter and terminator segments, is shown in FIG. 6.

Two additional 56-type vectors were constructed using a promoter fragment and promoter proximal region of the S-protein coding segment obtained from pHBS16-3 and from pHBS16-5. These constructions were designated pHBS56-3 and pHBS56-5, respectively. In both cases, an SphI-XbaI fragment was joined in a DNA ligase catalyzed reaction with the larger of the two SphI-XbaI fragments obtained by digestion of pHBS56. The larger fragment, approximately 1080 base pairs, extends from the XbaI site within the S-protein coding region to the SphI site of the ADH terminator region. This fragment was isolated by gel electrophoresis and electroelution prior to joining to the SphI-XbaI fragment of either pHBS16-3 or pHBS16-5, in a DNA ligase catalyzed reaction. The two composite genes thus constructed were identical except for the sequence of the 5'-untranslated region between the ADH promoter and the S-protein start codon, these differences arising from differences in the respective source vectors, pHBS16-3 and pHBS16-5 respectively. Both composite genes were subcloned, in separate reactions, at the SphI site of PBR322, situated between the BamHI site and the SalI site of PBR322, for the purpose of obtaining amplified amounts of composite gene DNA. The sub-cloning vectors were selected by their ability to confer ampicillin resistance and tetracycline sensitivity phenotype to E. coli. HB101 transformants.

Figure 7:
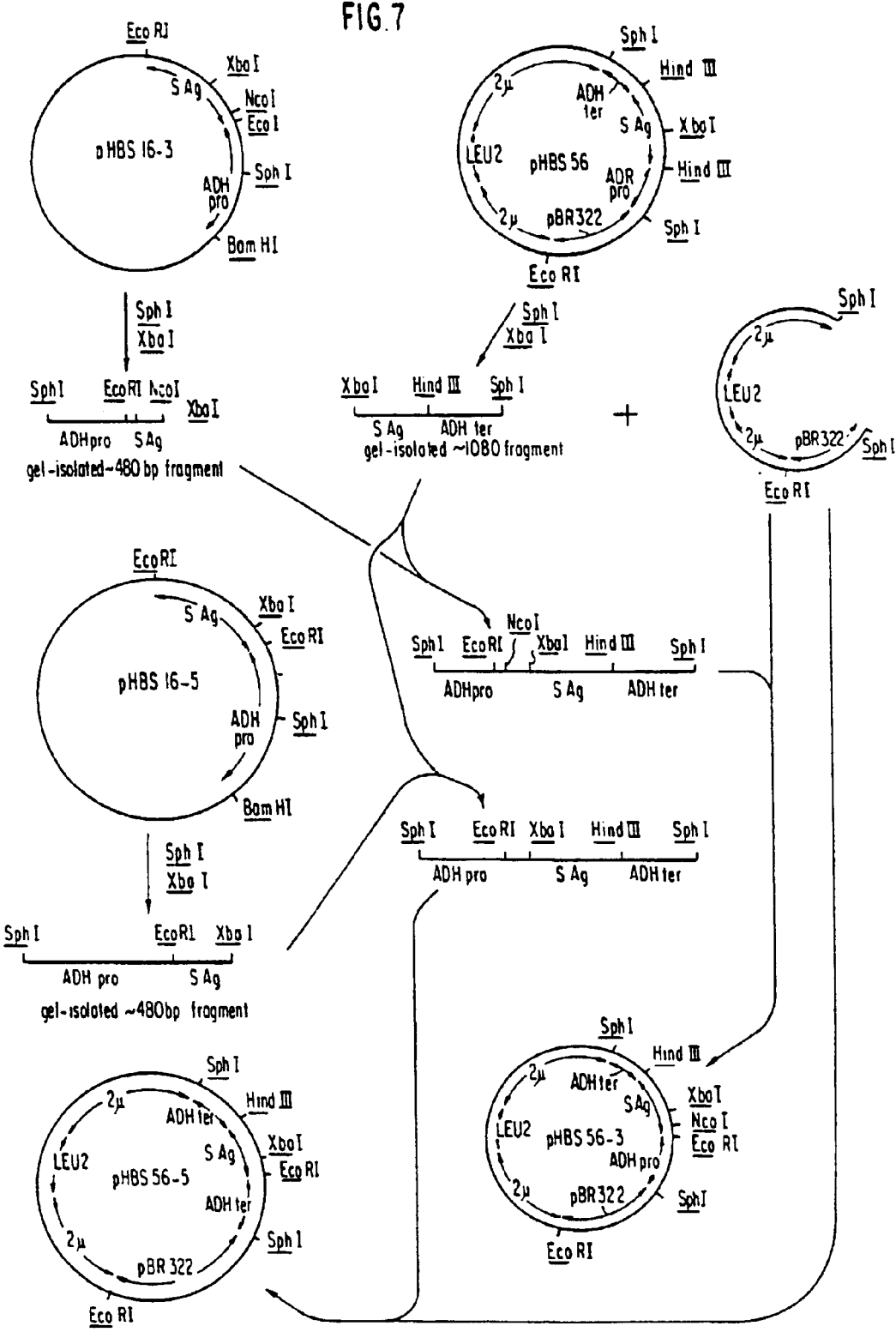
FIG. 7 shows the construction of plasmids pHBS 56-5 and pHBS56-3.

In the final step, the large fragment produced by SphI cleavage of pHBS56 was treated with alkaline phosphatase, and isolated by gel electrophoresis and electroelution. Similarly, the composite genes were excised from their sub-cloning vectors by SphI cleavage and isolated by gel electrophoresis and electroelution, but without phosphatase treatment. These were combined, in separate reactions, with the large SphI fragment of pHBS56 and joined in DNA ligase catalyzed reactions yielding pHBS56-3 and pHBS56-5, respectively. E. coli. HB101 transformants were selected by ampicillin resistance and tetracycline sensitivity and further characterized by restriction analysis. A diagram of the construction steps and,maps of the relevant vectors are shown in FIG. 7. Although the nomenclature of the 56 type vectors is parallel with that of the 16 type vectors, it will be understood that the distinctions in the case of the 56 series vectors refer only to the 5' untranslated region in each instance, and that the 3' untranslated region is the same in each member of the series. Specifically, pHBS56-3 lacks the 40 base pair deletion in the 3' untranslated region that occurs in pHBS-16-3.

After cloning selection and characterization, vectors of the 56 series were used to transform a circle zero yeast strain designated 2150-2-3. The strain was derived from a genetic cross between strain Y379-5-D cyh2 nib1 (rho⁻) Livingston, D. Genetics 86, 73 (1977) and DC 04 a AdeI AdeX leu2-04 (cir°) (Broach, J., Cell, 21, 501 (1980). The diploid strain resulting from the cross was permitted to sporulate and tetrads were disected by a standard procedure. One of the haploid spores gave rise to strain 2150-2-3 a AdeI Leu2-04 (cir°). Yeast transformants were selected for Leu⁺ phenotype conferred by the presence of plasmids of the pHBS-56 series.

The relative rates of Y-HBsAg expression in various plasmid-host combinations were compared in the following manner: A one liter volume of cell culture was grown to its limiting cell density, the cells harvested in crude lysates analyzed for total soluble protein and for Y-HBsAg, using radioimmuno-assay, as described, supra. The results were expressed both as micrograms Y-HBSAg per liter of culture and Y-HBsAg as percent by weight of total yeast soluble protein. The latter provides a measure of the amount of cell metabolism devoted to Y-HBsAg production while the former provides a measure of the overall yield of Y-HBsAg obtainable upon growth of cultures to limiting density. Differences arise particularly in the case of the 56 series vectors, because the cells carrying these vectors can be grown in rich media without selection pressure whereas the 16 and 25 series vectors require growth in a defined medium lacking tryptophan to prevent the accumulation of untransformed segregants. The results are shown in the accompanying table. The weights of Y-HBsAg given in the table were determined by a commercial radioimmunoassay using antibody raised against HBsAg. Therefore, the amounts of Y-HBsAg reported may not be an absolute measure of mass but may he considered to be internally consistent for purposes of comparison.

Y-HBsAg Yields

| Vector pHBS- | Host | Culture Density O.D.$_{660}$ | % by weight of total yeast soluble protein | µg Y-HBsAg per liter culture |
|---|---|---|---|---|
| 16-3 | AB-35-14D | 2.0 | 0.1% | 20 |
| 16-4 | AB-35-14D | 2.0 | 0.1% | 20 |
| 16-5 | AB-35-14D | 2.0 | 0.1% | 20 |
| 25 | GM-3C-2 | 4.0 | 0.5% | 200 |
| 56 | 2150-2-3 | 12.0 | 0.3% | 300 |

EXAMPLE 7

Preparation of a Vaccine Comprising HBsAg Synthesized by Yeast

Y-HBsAg particles are purified from cell extracts by the method of Example 3, or by suitable methods known in the art. for example, as described in U.S. Pat. Nos. 4,088,748 or 4,181,713. Purified HBsAg particles are dialyzed against physiological saline or phosphate-buffer saline and adjusted to 100 µg protein/ml final contentration. Guinea pigs are subjected subcutaneously at 9, 14 and 56 day intervals with 1 ml of the HBsAg preparation. The serum of the test animals is sampled at 0, 28, 56 and 84 days and assayed for antibody titre agaist Dane particles or HBsAg purified from Alexander cells. The radioimmune assay described in Example 3 is employed, or in the alternative, the radioimmunoassay of Hollinger, F. et al., *J. Immunol.* 107, 1099 (1971) is employed. The majority of animals exhibit antibodies cross-reactive with HBsAg 84 days after administration of the particles. Similar results are obtained upon injection of monkeys. Accordingly, HBSAg synthesized by yeast is immunogenic and is capable of eliciting antibodies cross-reactive with naturally-occurring HBsAg.

HBsAg synthesized by yeast has the advantage of being available in significantly larger quantities than that obtained from Dane particles or carrier serum. A more uniform product is obtainable at an advantageous cost per unit, which may be expected to decrease with increasing production volume. Furthermore, Furthermore, thre is no danger of accidental infection, since there is no intact HBV, and can be no intact HBV, in the surface antigen prepared from yeast. By contrast, viral proteins purified from serum or other natural sources always pose the danger of viral cotamination.

EXAMPLE 8

As shown in Exmple 7, HBsAg synthesized by yeast is capable of eliciting antibodies cross-reactive with naturally-occurring HBsAg. It therefore follows that such antigens and antigen aggregates, when purified as described and administered in a physiologically acceptable medium, constitute a vaccine for protection agaist infection by hepatitis B virus.

Sixteen chimpanzees are divided into three groups. Group A (six animals) is inoculated intravenously with 1 ml of a standard Bureau of Biologics Hepatitis B virus preparation; Group B (four animals) is inoculated intravenously with 1 ml containing 200 µg of HBsAg synthesized in yeast and purified as described in Example 3, in physiological saline; Group C (six animals) is the control group and receives no inoculation. All chimps in Group A have evidence of clinical Hepatitis B (either antigenemia, enzyme elevations and/or antibody response) within 40 weeks. None of the animals in Groups B or C shows evidence of clinical Hepatitis B infection over the same 40-week period. The chimps of Group B are rendered immune to subsequent challenge when inoculated intravenously with 1.0 ml of BOB Hepatitis B virus.

EXAMPLE 9

Y-HBsAg differed in several respects from plasma-derived HBsAg. The diameters of HBsAg and Y-HBsAg particles were measured from negatively stained electron micrographs. The yeast-derived antigen had a diameter range of from about 14 to about 18 nm while plasma-derived antigen had a diameter range of from about 20 to about 24 nm.

Y-HBsAg was unstable at pH 2, and to pepsin at pH 2, whereas plasma-derived HBsAg was stable under the same conditions. To a 1 ml suspension of purified Y-HBsAg was added 0.03 ml of 1N HCl to lower the pH to 2.0. The sample was divided in halves and to one-half was added 1 µg of pepsin while no enzyme was added to the other half. Both samples were held at 37° C. for sixteen hours and then 0.03 ml of 1N Naoh was added to each to raise the pH to 7.0. The two samples were measured for antigen binding activity in a quantitative radioimmunoassay (RIA). Over 95% of the RIA activity was lost in each sample. Under the same conditions the plasma derived HBsAg retained all of its antigen binding activity.

A sample of purified Y-HBsAg was heated in sodium dodecylsulfate (SDS) and 2-mercaptoethanol at 90° C. for five minutes. It was then electrophoresed through a 10% polyacrylamide gel containing 0.1% SDS. Subsequent staining of the gel with protein, stains revealed a single band at a molecular weight equivalence location of about 25,000. A plasma purified HBSAG sample treated identically showed two bands after staining: one band at about 25,000 daltons and a second band at about 28,000 daltons.

Unlike plasma-derived HBsAg, Y-HBsAg did not bind to a monoclonal antibody (HBsAb) selected against HBsAg. A crude extract of yeast cells containing surface antigen was passed through an affinity adsorbent column prepared by chemically coupling monoclonal HBsAb to an agarose gel. Measurement of the column effluent revealed 90% of the Y-HBsAg charged to the column was present in the effluent. A plasma-derived HBsAg passed through the same column of monoclonal HBsAb revealed less than 10% of the charged antigen in the column effluent.

Y-HBsAg exhibited higher activity in mouse potency tests. Y-HBsAg was adsorbed to an aluminum hydroxide gel prior to administration and was diluted to contain 10, 2.5, 0.62, 0.15 and 0.0375 µg/ml. 1 M1 quantities of the foregoing concentrations were injected intraperitoneally into each of five groups of five-week old female mice. Each of these concentrations was injected into one of the five groups, each group containing ten mice. The yeast-produced antigen had an $ED_{50}$ (the concentration of antigen needed to produce antibody in one-half of the mice) of about 0.05 µg/ml while the plasma-derived antigen in the same procedure had an $ED_{50}$ of about 0.5 µg/ml.

Y-HBsAg purified as described was essentially free of contaminating chemicals. Measurement of the Lowry protein of Y-HBsAg showed 53 µg/ml while measurement of the RIA antigen binding ability of this antigen indicated a concentration of 12 µg/ml. Measurement of the Lowry protein and RIA antigen binding ability of a pure preparation of plasma-derived HBsAg revealed a protein concentration of 44 µg/ml and a binding activity of 50 µg/ml.

No differences were observed in the physical, chemical or antigenic properties of Y-HBsAg produced from cells tranformed with pHBs-16, -25 or -52.

EXAMPLE 10

Comparative Study of Potency in Mice of Yeast-Derived Antigen with Plasma-derived Antigen A total of 80 five-week old female mice were divided into two groups of 40 and each group was further subdivided into four sub-groups of 10 mice. The 10 mice from each sub-group were injected intraperitoneally with either the antigen prepared from Example 3 using vector pHBS-25 or plasma-derived antigen at a concentration, respectively, of 10, 2.5, 0.625 or 0.156 µg/ml. Saline-alum placebo was used as diluent to dilute the antigen concentration where necessary to obtain the foregoing concentrations. The mice were individually bled and sacrificed at 28 days. Antibody determinations were performed by the Ausab (Abbott) radioimmune assay. The serological results are summarized in the following table wherein titers are expressed as "Estimated Ausab Units".

| Group | Material | Conc. (µ/ml) | Sero-Conversion | Anti-HBs Titer Estimated Ausab Units |
|---|---|---|---|---|
| I | Yeast-Derived Antigen | 10 (RIA) | 10/10 | 5400, 7200, 800, 13,500, 7200, 183, 800, 136,000, 15,800, 23,500 |
| II | | 2.5 | 10/10 | 18,300, 5400, 800, 7200, 5400, 800, 5400, 1600, 135,000, 72 |
| III | | 0.625 | 8/10 | 800, 8, 1600, 16,000, 158,000, 1600, 3600, 8, 8, 8000 |
| IV | | 0.125 | 8/10 | 8, 800, 800, 32,200, 5400, 8, 112,000, 18,300, 477, 412 |
| V | Plasma-Derived Antigen | 10 (Lowry) | 9/10 | 292,000, 20,800, 8, 38,200, 16, 16, 13,500, 36, 54, 512 |
| VI | | 2.5 | 10/10 | 36, 38,200, 15,800, 800, 800, 800, 7200, 18,300, 208, 15,800 |
| VII | | 0.625 | 4/9 | 8, 8, 8, 800, 512, 512, 8, 158, 8 |

-continued

| Group | Material | Conc. (µ/ml) | Sero-Conversion | Anti-HBs Titer Estimated Ausab Units |
|---|---|---|---|---|
| VIII | | 0.125 | 0/10 | 8, 8, 8, 8, 8, 8, 8, 8, 8, 8 |

EXAMPLE 11

Comparative Study of Potency in African Green Monkeys of Yeast-Derived Antigen with Placebo Derived Antigen A total of 32 African Green Monkeys were divided into two groups of 16, and each group was further subdivided into four sub-groups of 4 monkeys. Each sub-group was injected intramuscularly at day 0 and day 28 with yeast-derived antigen or plasma-derived antigen at a concentration, respectively, of 10, 2.5, 0 625 or 0.156 µg/ml using saline-alum placebo as diluent to dilute the antigen concentration where necessary to obtain the foregoing concentrations. Bleedings were collected at weekly intervals for 14 weeks and antibody determinations were performed by the Ausab (Abbott) radioimmune assay with titers expressed as "Estimated Ausab Units". The results are summarized in the following tables.

| | | (Yeast-Alum) | | | | | | | |
|---|---|---|---|---|---|---|---|---|---|
| | Conc. | Time/Week/Estimated Ausab Units | | | | | | | |
| Animal # | (mcg/ml) (RIA) | −1 | 0* | 2 | 4* | 6 | 8 | 10 | 12 | 14 |
| v-80015 | 10 | <8 | <8 | 54 | 36 | 322 | 5400 | 3600 | 1600 | 2350 |
| 79144 | 10 | <8 | <8 | 920 | 112 | 135 | 292 | 5120 | 20,800 | 20,200 |
| 79147 | 10 | <8 | <8 | 72 | 72 | 135 | 4120 | 13,500 | 29,200 | 26,200 |
| 80012 | 10 | <8 | <8 | 512 | 208 | 135 | 208 | 3520 | 2620 | 47,700 |
| v-80006 | 2.5 | <8 | <8 | 512 | 352 | 3220 | 36,000 | 54,000 | 72,000 | 16,000 |
| 79148 | 2.5 | <8 | <8 | 512 | 112 | 92 | 112 | 92 | 135 | 512 |
| 80009 | 2.5 | <8 | <8 | 382 | 112 | 158 | 183 | 5120 | 29,200 | 32,200 |
| 80016 | 2.5 | <8 | <8 | 720 | 262 | 5120 | 800 | 20,800 | 18,300 | 23,500 |
| v-80185 | 0.625 | <8 | <8 | 183 | 412 | 5120 | 8000 | 16,000 | 20,800 | 20,800 |
| 80192 | 0.625 | <8 | <8 | 7200 | 158 | 92 | 158 | 5120 | 18,300 | 11,200 |
| 80193 | 0.625 | <8 | <8 | 5400 | 352 | 5120 | 16,000 | 13,500 | 18,300 | 26,200 |
| 80201 | 0.625 | <8 | <8 | 183 | 112 | 112 | 92 | 112 | 235 | 442 |
| v-80181 | 0.156 | <8 | <8 | 512 | 352 | 2920 | 5400 | 1600 | 1350 | 1350 |
| 80178 | 0.156 | <8 | <8 | 477 | 262 | 158 | 92 | 92 | 12 | 5120 |
| 80180 | 0.156 | <8 | <8 | <8 | <8 | 5400 | 1600 | 360 | 360 | 720 |
| 80175 | 0.156 | <8 | <8 | <8 | 382 | 3220 | 920 | 360 | 360 | 360 |

| | | (Plasma) (Alum) | | | | | | | |
|---|---|---|---|---|---|---|---|---|---|
| | Conc. (mcg/ | Time/Week/Estimated Ausab Units | | | | | | | |
| Animal # | ml) (Lowry) | −1 | 0* | 2 | 4* | 6 | 8 | 10 | 12 | 14 |
| v-80176 | 10 | <8 | <8 | <8 | <8 | <8 | <8 | 8 | <8 | 8 |
| 80182 (A) | 10 | <8 | <8 | 512 | 512 | 5120 | 36,000 | 16,000 | 7200 | 3600 |
| 80179 | 10 | <8 | <8 | 8 | 208 | 5120 | 3600 | 3220 | 7200 | 11,200 |
| 80177 | 10 | <8 | <8 | <8 | <8 | 16 | <8 | <8 | <8 | <8 |
| v-79142 | 2.5 | <8 | <8 | 512 | 292 | 512 | 38,200 | 8000 | 20,800 | 23,500 |
| 80035 | 2.5 | <8 | <8 | 512 | 352 | 92 | 135 | 5120 | 5400 | 5400 |
| 78089 | 2.5 | <8 | <8 | <8 | 262 | 5120 | 5400 | 5400 | 7200 | 7200 |
| 80120 | 2.5 | <8 | <8 | 512 | 512 | 5120 | 54,000 | 16,000 | 11,200 | 7200 |
| v-78151 | 0.625 | <8 | <8 | <8 | <8 | 512 | 7200 | 5400 | 5400 | 3600 |
| 79149 | 0.625 | <8 | <8 | <8 | 477 | 1830 | 1120 | 1830 | 3220 | 7200 |
| 80182 (B) | 0.625 | <8 | <8 | <8 | 8 | 5120 | 1600 | 720 | 360 | 540 |
| 79143 | 0.625 | <8 | <8 | 235 | 512 | 5120 | 36,000 | 16,000 | 16,000 | 32,200 |

-continued

| | | | | | | | | | | |
|---|---|---|---|---|---|---|---|---|---|---|
| v-79140 | 0.156 | <8 | <8 | <8 | 16 | 183 | 72 | 183 | 352 | 5120 |
| 79146 | 0.156 | <8 | <8 | <8 | <8 | 1600 | 360 | 36 | 36 | 72 |
| 77024 | 0.156 | <8 | <8 | 512 | 208 | 1600 | 2620 | 800 | 920 | 540 |
| 80155 | 0.156 | <8 | <8 | <8 | <8 | <8 | <8 | <8 | <8 | D |

*Inoculate - 1.0 ml i.m. at day 0, 4 weeks
D = Died

GENERAL CONCLUDING REMARKS

The present invention represents a substantial advance in applying recombinant DNA technology. The practical goal of synthesizing HBsAg in a microorganism host has been achieved. Modifications to increase HBsAg production and improve the yield of HBsAg upon purification, which fall within the scope of ordinary skill in the art, are deemed equivalent variants within the scope of the claimed invention. Examples of such modifications could include improved promoter systems, more productive host cell strains, improvements in purification technique and modifications to improve the antigenicity of the product or its immunogenicity.

Although the microorganism employed in these studies was yeast, any eucaryotic microorganism is considered to be capable of serving as a host strain for producing HBsAg particles, provided a sufficient amount of antigen is synthesized thereby. Examples of othr eucaryotic microorganisms which could be employed include, but are not limited to, members of the genera aspergillus, penicillium, and neurospora, as well as the genus Saccharomyces.

The following plasmids and transformed yeast strains were deposited with the American Type Culture Collection, 12301 Parklawn Drive, Rockville, Md. 20852, USA.

| Description | Deposit date | Accession No. |
|---|---|---|
| 1. Plasmid pHBS-16 | Aug. 4, 1981 | 40043 |
| 2. *S cerevisiae* XV610-8C/ pHBS-16 | Aug. 4, 1981 | 20619 |
| 3. Plasmid pHBS56 | Jul. 7, 1982 | 40047 |
| 4. Plasmid pHBS16-3 | Jul. 7, 1982 | 20647 |
| 5. *S. cerevisiae* AB 35-14D/ pHBS16-3 | Jul. 7, 1982 | |
| 6. *S. cerevisiae* AB35-14D/ pHBS16-4 | Jul. 7, 1982 | 20648 |
| 7. *S. cerevisiae* 2150-2-3/ pHBS56 | Jul. 7, 1982 | |
| 8. Plasmid pHBS16-4 | Jul. 7, 1982 | 40046 |
| 9. Plasmid pHBS16-5 | Jul. 7, 1982 | 40045 |
| 10. *S. cerevisiae* AB35-14D/ pHBS16-5 | Jul. 7, 1982 | 20645 |
| 11. Plasmid pHBS56-3 | | |
| 12. Plasmid pHBS56-5 | | |
| 13. *S. cerevisiae* 2150-2-3/ pHBS56-3 | | |
| 14. *S. cerevisiae* 2150-2-3/ pHBS56-5 | | |

The depository was requested to handle the above-described deposits in accordance with the terms and conditions of the Budapest Treaty on the International Recognition of the Deposit of Microorganisms for the Purposes/ Patent Procedure.

What is claimed is:

1. Mature hepatitis B surface antigen in particle form produced by a process which comprises transformation of yeast with a DNA segment encoding said mature hepatitis B surface antigen, wherein said particle consists of mature hepatitis B surface antigen that has a sedimentation rate virtually identical to that of authentic 22 nm hepatitis B surface antigen particles.

2. A method of immunizing a primate against Hepatitis B virus infection comprising administering to said primate a vaccine comprising hepatitis B surface antigen in particle form produced from yeast that expressed a DNA segment encoding mature hepatitis B surface antigen, wherein said surface antigen particle consists of mature hepatitis B surface antigen that has a sedimentation rate virtually identical to that of authentic 22 nm hepatitis B surface antigen particles.

3. A vaccine for protecting a primate against Hepatitis B virus infection, the vaccine comprising a pharmaceutical excipient suitable for a primate and hepatitis B surface antigen in particle form produced from yeast that expressed a DNA segment encoding mature hepatitis B surface antigen, wherein said surface antigen particle consists of mature hepatitis B surface antigen that has a sedimentation rate virtually identical to that of authentic 22 nm hepatitis B surface antigen particles.

* * * * *